United States Patent
Gautham et al.

(10) Patent No.: US 7,158,891 B2
(45) Date of Patent: Jan. 2, 2007

(54) METHOD AND SYSTEM TO BUILD OPTIMAL MODELS OF 3-DIMENSIONAL MOLECULAR STRUCTURES

(75) Inventors: Namasivayam Gautham, Tamil Nadu (IN); Krishnan Vengadesan, Tamil Nadu (IN)

(73) Assignee: Council of Scientific & Industrial Research, New Delhi (IN)

( * ) Notice: Subject to any disclaimer, the term of this patent is extended or adjusted under 35 U.S.C. 154(b) by 78 days.

(21) Appl. No.: 10/113,219

(22) Filed: Mar. 28, 2002

(65) Prior Publication Data

US 2003/0187585 A1    Oct. 2, 2003

(51) Int. Cl.
*G01N 33/48* (2006.01)
*G06G 7/48* (2006.01)

(52) U.S. Cl. .............................. 702/20; 702/19; 703/2; 703/11; 703/12; 707/102; 708/207

(58) Field of Classification Search .................... 703/2, 703/11, 12; 707/102; 708/207
See application file for complete search history.

(56) References Cited

U.S. PATENT DOCUMENTS

| | | | |
|---|---|---|---|
| 5,884,230 A | 3/1999 | Srinivasan et al. | 702/22 |
| 6,188,956 B1 | 2/2001 | Walters | 701/200 |
| 6,188,965 B1 | 2/2001 | Mayo et al. | 702/27 |

FOREIGN PATENT DOCUMENTS

WO    WO 99 26901 A    6/1999

OTHER PUBLICATIONS

S. Schulze-Kremer, *Methods in Molecular Biology*, 2000, 13:176-222.
N. Gauthan et al., *Current Science*, 1992, p. 560-564.
K.D. Gibson et al., *J. of Computational Chem.*, 1987, 8(6)826-834.
L. Piela et al., *Biopolymers*, 1987, 26:33-58.
Z. Li et al., *Proc. Natl. Acad. Sci.*, 1987, 84:6611-6615.
D.R. Ripoli et al., *Biopolymers*, 1998, 46:117-126.
L. Piela et al., *J. Phys. Chem.*, 1989, 93:3339-3346.
J. Pillardy et al., *J. Phys. Chem.*, 1995, 99(31)11805-11812.
J. Lee et al., *Biopolymers*, 1998, 46:103-115.
A. Liwo et al., *Proc. Natl. Acad. Sci.*, 1999.
D. Cvijovic et al., *Science*, 1995, 267:664-666.
J. Brethen et al., *Science*, 1997, 276:1094-1097.
J.F. Griffen et al., *Proc. Natl. Acad. Sci.*, 1986, 83:3272-3276.
E. Benedetti et al., *J. Amer. Chem. Soc.*, 1982, 104(9):2437-2444.
N. Shamala et al., *J.C.S. Chem. Comm.*, 1978, 22:996-997.
Gautham et al., *Current Science*, 1992, 63:560-564.
Johnson et al., *Canadian J. of Mathematics*, 1961, 13:356-372.
PCT Search Report.

*Primary Examiner*—Mary K. Zeman
(74) *Attorney, Agent, or Firm*—Morgan & Finnegan, LLP (57) ABSTRACT

The present invention relates to a method to build 3-dimensional models of molecular structures corresponding to the lowest value of the potential energy function from knowledge of their chemical structures. The system uses Mutually Orthogonal Latin Squares to search through conformational space to obtain the best conformation. The system may also be used to obtain the optimum of any function, and not only those related to biomolecular structure.

5 Claims, 9 Drawing Sheets

Figure 1

| a1  b1
c1 | a2  b2
c2 | a3  b3
c3 | a4  b4
c4 | a5  b5
c5 | a6  b6
c6 | a7  b7
c7 |
|---|---|---|---|---|---|---|
| a2  b7
c6 | a3  b1
c7 | a4  b2
c1 | a5  b3
c2 | a6  b4
c3 | a7  b5
c4 | a1  b6
c5 |
| a3  b6
c4 | a4  b7
c5 | a5  b1
c6 | a6  b2
c7 | a7  b3
c1 | a1  b4
c2 | a2  b5
c3 |
| a4  b5
c2 | a5  b6
c3 | a6  b7
c4 | **a7  b1
c5** | a1  b2
c6 | a2  b3
c7 | a3  b4
c1 |
| a5  b4
c7 | a6  b5
c1 | a7  b6
c2 | a1  b7
c3 | a2  b1
c4 | a3  b2
c5 | a4  b3
c6 |
| a6  b3
c5 | a7  b4
c6 | a1  b5
c7 | a2  b6
c1 | a3  b7
c2 | a4  b1
c3 | a5  b2
c4 |
| a7  b2
c3 | a1  b3
c4 | a2  b4
c5 | a3  b5
c6 | a4  b6
c7 | a5  b7
c1 | a6  b1
c2 |

Figure 7
Flow Chart

METHOD AND SYSTEM TO BUILD OPTIMAL MODELS OF 3-DIMENSIONAL MOLECULAR STRUCTURES

FIELD OF THE INVENTION

The present invention relates to a method to build 3-dimensional models of molecular structures corresponding to the lowest value of the potential energy function from knowledge of their chemical structures. The present invention specifies a method that may be used to build a model of the three-dimensional structure of any molecule including, but not limited to, peptides, proteins, nucleotides, nucleic acids, antibiotics, saccharides, etc. The system uses Mutually Orthogonal Latin Squares to search through conformational space to obtain the best conformation. The system may also be used to obtain the optimum of any function, and not only those related to biomolecular structure. The method is incorporated into a computer and this system forms the present invention.

BACKGROUND OF THE INVENTION

U.S. Pat. No. 5,884,230 to Srinivasan et al. titled 'Method and system for protein modeling' discloses a method in a computer system for modeling a three-dimensional structure of a model protein in which the modeling is based upon a three-dimensional structure of a template protein and an amino acid sequence alignment of the model protein and the template protein. For each amino acid in the model protein, when the template protein has an amino acid aligned with the amino acid of the model protein, the position of the backbone atom of the amino acid aligned with the amino acid of the model protein is established based on the position of a topologically equivalent backbone atom in the aligned amino acid of the template protein. However, this method works only when the structure of a model protein is already known. Therefore it is not applicable to smaller molecules such as oligopeptides, or to molecules that are chemically different, such as nucleic acids, saccharides, antibiotics, and other organic molecules. Even in the case of protein structure, the method is not applicable to ab initio protein structure determination, in other words, the method cannot be applied if there is no model structure from which to start.

U.S. Pat. No. 6,188,956 to Mayo, et al. titled 'Apparatus and method for automated protein design' relates to an apparatus and a methods for quantitative protein design and optimization. The method receives a known protein backbone structure and builds the conformations of the side chains using the Dead-End Elimination method. As above, this method also would work only when the structure of a model protein is already known. Therefore it is not applicable to smaller molecules such as oligopeptides, or to molecules that are chemically different, such as nucleic acids, saccharides, antibiotics, and other organic molecules. Even in the case of protein structure, the method not applicable to ab initio protein structure determination, in other words, if there is no model structure from which to start, the method cannot be applied since it requires an already known protein backbone conformation.

'Combinatorial Mathematics', H. J. Ryster, a textbook of combinatorial mathematics gives a definition of Mutually Orthogonal Latin Squares together with an equation to construct them. However, there is no explanation of how the equation is to be incorporated into a computer program. Also there is no mention of any application of Mutually Orthogonal Latin Squares (MOLS) to find the best value of any function, including the potential energy function. Also there is no mention of any application to the determination of the three-dimensional structure of a molecule. Also it only describes how to distribute a set of symbols so as to form a set of MOLS, but it does not describe any method to replace the symbols with the values of the parameters that define any function. Also it does not describe how the calculations are to be analyzed after the construction of the MOLS.

'Introduction to Combinatorial Mathematics', by C. L. Liu is another textbook reference on combinatorial mathematics which gives a definition of Mutually Orthogonal Latin Squares together with an equation to construct them. Again however, there is no explanation of how the equation is to be incorporated into a computer program. Also there is no mention of any application of Mutually Orthogonal Latin Squares (MOLS) to find the best value of any function, including the potential energy function. Also there is no mention of any application to determination of the three-dimensional structure of a molecule. Also it only describes how to distribute a set of symbols so as to form a set of MOLS, but it does not describe any method to replace the symbols with the values of the parameters that define any function. Also it does not describe how the calculations are to be analyzed after the construction of the MOLS.

'Experimental Design and Its Statistical Basis', D. J. Finney is a textbook on experimental design which gives a method to use Mutually Orthogonal Latin Squares in agricultural and pharmaceutical experiments. However, there is no teaching herein of how MOLS are to be constructed, nor does it specify any computer program to do so, nor does it mention any application to determine molecular structure or to find the best value of a function. Also the analyses of the calculations made in each sub square as stated in this book are more complicated than the one used in the present invention.

'Genetic Algorithms and Protein Folding' by S. Schulze-Kremer, Methods in Molecular Biology (D Webster, ed.) 2000 describes the application of genetic algorithms in protein structure prediction. However, the method described fails for ab initio structure prediction. That is, if there is no previous information about the secondary structure, the method does not work. Also the method does not use MOLS in any form in the calculations, and hence is different from the present invention. 'Global Search for Optimal Biomolecular Structures using Mutually Orthogonal Latin Squares' by N. Gautham and Z. A. Rafi, Current Science, 1992 is a very preliminary report of the possible use of MOLS in structure prediction. The method was however, crude and not properly formulated. It did not incorporate any equation to predict MOLS, and it did not specify how the symbols of the MOLS are to be related to the values of the variables. It did not specify in detail the method used for analyzing the values calculated in the sub squares. It was not applied to pentapeptides.

'Revised algorithms for build-up procedure for predicting protein conformations by energy minimization' by K. D. Gibson and H. A. Scheraga, Journal of Computational Chemistry, 1987 discloses 'Build-Up Procedure' to predict protein conformations. This method carries out a truncated search, relaying on the dominance of short-range interactions. Thus, it finds local minima for short fragments by an exhaustive energy-minimization procedure. The number of conformations for the fragments that must be energy minimized and stored at each step increases exponentially. The method becomes unmanageable for polypeptide chains of about 20 amino acid residues. Also there is no mention at all of the use of MOLS in any form in the procedure. 'On the multiple-minima problem in the conformational analysis of polypeptides' I. Backbone degrees of freedom for a perturbed a-helix' by L. Piela and H. A. Scheraga, Biopolymers, 1987 discloses the use of a 'Self Consistent Electrostatic Field', based on the idea that a peptide group dipoles in a native conformation must have an approximately optimal orientations in the electric field generated by the whole molecule and its surrounding solvent. The method does not use all the other energy terms, It is therefore specific for only the an electrostatic field. It cannot be applied to small molecules such as peptides, etc. Also there is no mention at all of the use of MOLS in any form in the procedure.

'Monte Carlo-Minimization approach to the multiple-minima problem in protein folding' by Z. Li and H. A. Scheraga, Proceedings of the National Academy of Sciences, 1987 discloses a stochastic approach for global optimization of polypeptides and proteins that combines the strength of the Metropolis Monte Carlo method in global combinatorial optimization with that of conventional energy minimization to find local minima. This is not a deterministic search procedure and therefore will not ensure the best structure every time. Also it is very computationally intensive and therefore very expensive in terms of computer time. Also there is no mention at all of the use of MOLS in any form in the procedure and hence this method is different from the present invention. 'New developments of the electrostatically driven Monte Carlo method—Test on the membrane bound portion of melittin' by D. R. Ripoll, A. Liwo and H. A. Scheraga, Biopolymers, 1998 discloses an iterative procedure for searching the conformational hypersurface of polypeptides. This is not a deterministic search procedure and therefore will not ensure the best structure every time. Also it is very computationally intensive and therefore very expensive in terms of computer time. Also there is no mention at all of the use of MOLS in any form in the procedure.

'The multiple-minima problem in the conformational analysis of molecules—Deformation of the potential energy hypersurface by the diffusion equation method', L. Piela, J. Kostrowicki and H. A. Scheraga, Journal of Physical Chemistry, 1989 discloses the use of the basic idea of the 'Diffusion Equation Method' to deform the multivariable function that represents the potential energy in such a manner as to make the shallow wells disappear gradually, while other potential wells grow at their expense. The method is not easily applied in practice to complicated structures. This is not a deterministic search procedure and therefore will not ensure the best structure every time. Also it is very computationally intensive and therefore very expensive in terms of computer time. Also there is no mention at all of the use of MOLS in any form in the procedure.

'Molecular dynamics on deformed potential energy hypersurfaces' by J. Pillardy and L. Piela, Journal of Physical Chemistry, 1995. The 'Distance Scaling Method' is a procedure to deform the potential energy hypersurface. The procedure is an extension of the 'diffusion equation method' and suffers from the same drawbacks. This is not a deterministic search procedure and therefore will not ensure the best structure every time. Also it is very computationally intensive and therefore very expensive in terms of computer time. Also there is no mention at all of the use of MOLS in any form in the procedure.

'Conformational analysis of the 20-residue membrane-bound portion of melittin by conformational space annealing' by J. Lee and H. A. Scheraga, Biopolymers, 1998 combines essential aspects of the build-up procedure and a genetic algorithm. It searches the whole conformational space in its early stages and then narrows the search to smaller regions of low energy. However, searching the entire conformational space requires large amounts of computer time. Therefore it is very computationally intensive and very expensive in terms of computer time. Also there is no mention at all of the use of MOLS in any form in the procedure.

'Protein structure can be predicted by global optimization of a potential energy function' by A. Liwo, J. Lee, D. R. Ripoll, J. Pillardy and H. A. Scheraga, Proceedings of the National Academy of Sciences, 1999 uses a Hierarchical Approach based on two recent developments, a united-residue force field (UNRES) and the CSA method. An extensive conformational search is carried out with CSA using a UNRES force field. This suffers from the same drawbacks as the 'Conformational space Annealing method'. In other words, it is very computationally intensive and therefore very expensive in terms of computer time. Also there is no mention at all of the use of MOLS in any form in the procedure.

'Taboo Search: An approach to the Multiple Minima Problem', D. Cvijiovic and J. Klinowski, Science, 1995 describes a method, Taboo Search (TS), based on the Glover's taboo search for discrete functions, of solving the multiple minima problem for continuous functions. The method does not indicate any application to molecular structure. Also it is very computationally intensive and therefore very expensive in terms of computer time. Also there is no mention at all of the use of MOLS in any form in the procedure.

'TRUST: A deterministic algorithm for Global Optimization' by J. Barthen, V. Protopopescu and D. Reister, Science, 1997 suggests an approach the use of Terminal Repeller Unconstrained Sub-energy Tunneling algorithm (TRUST) to solve continuous global optimization problems. The method, however, does not indicate any application to molecular structure and is also very computationally intensive. Therefore the method is expensive in terms of computer time. Also there is no mention of the use of MOLS in the procedure.

OBJECTS OF THE INVENTION

The main object of the present invention is to provide a method to build optimal 3-dimensional models of molecular structures from knowledge of their chemical structures, which obviates the above-mentioned drawbacks, as detailed below.

Another object of the present invention is to provide a method and a system to build minimum-energy structures of biological macromolecules such as proteins and nucleic acids.

Another object of the present invention is to apply the method of the invention to find the best value of a function.

Another object of the present invention is to apply the method of the invention to find the best value of a potential energy function of a molecule.

Another object of the present invention is to make the method of structure determination simple and straightforward and inexpensive, in terms of computer time, to use.

Another object of the present invention is to apply the method of the invention to a wide variety of problems in which a physical or chemical system is defined as a function of a set of parameters and the invention is used to find the best configuration of the system by finding the best set of values of the parameters which give the best value of the function.

Another object of the present invention is to provide a method which can be easily be combined with other known methods such as gradient search, simulated annealing, etc.

Another object of the present invention is to make it easily programmable to run on parallel computers, thus saving valuable time.

SUMMARY OF THE INVENTION

Accordingly the present invention provides a method for determining the lowest value of the conformational potential energy function of a molecule, the method being useful for modeling a 3-dimensional molecular structure by using a new algorithm to define the best conformation as the one corresponding to the lowest value for the conformational potential energy function, said method comprising the steps of:

a) representing a molecule by a set of coordinates of the atoms comprising the molecule;

b) selecting a set of conformations from all possible conformations obtained from a combinatorial arrangement of n Mutually Orthogonal Latin Squares (MOLS) of order N, constructed from the conformational parameters in the molecule, resulting in $N^2$ sub squares for each set of MOLS, wherein N is equal to n or m, whichever is larger, with n being number of a conformational parameter defining the conformation of the molecule and m being the number of values sampled along each conformational parameter and the step size being R/m, with R being the range of the parameter, and each MOLS sub square corresponding to one possible conformation of the said molecule;

c) filling up the sub squares of the MOLS with conformations of the said molecule, with one conformation in each sub square, the conformation in any given sub square being represented by the values of the conformational parameters in that sub square;

d) choosing the values of the conformational parameters in the sub squares by first specifying the number of parameters, n, and the range of each of the n parameters, and the step size at which the values of each parameter is sampled, there being a total of m steps along each parameter, so that $\theta_{r,s}$, r=1 to n and s=1 to m are specified as the input set of values for the conformational parameters;

e) labeling the sub squares of the said MOLS by indices (u,t), u and t being integer numbers, u=1 to N and t=1 to N, and the value of the rth torsion angle in a given sub square (u,t) being chosen from the input set of values $\theta_{r,s}$ as $\theta^r_{u,t} = \theta_{r,s}$, in which the index u is given by u={(t−1) (r−1)+(s−1)} modulo(N);

f) repeating the procedure of filling up the sub squares with the values of the parameters chosen for all values of r=1 to n, s=1 to 11, and t=1 to N, with u being calculated each time by the formula given in claim 4, by which at the end of the procedure, each sub square of the $N^2$ sub squares of the said MOLS will be filled with a set of n values, each value corresponding to one of the n conformational parameters, thus the set of n values in each sub square defining one conformation of the said molecule, there being $N^2$ conformations;

g) calculating the potential energy function by known methods for each of $N^2$ conformations of the said molecule as represented in the $N^2$ sub squares of the said set of MOLS, these functions being represented as $$V_{u,t} = V(\theta^r_{u,t}),$$

h) analyzing the set of $N^2$ values of the potential energy function in order to determine the best value of each conformational parameter;

i) analysing by determining the average value of the potential energy function for each value of each parameter, by taking the average of the values of the potential energy function at all the N conformations where that value of the conformational parameter is used in defining the conformations, there being thus n×m average values, the average values being given by:

$$\langle V \rangle^r_s = \frac{\sum_t V(\theta^r_{u,t}) \exp(-V(\theta^r_{u,t})/kT)}{\sum_t \exp(-V(\theta^r_{u,t})/kT)};$$

j) scanning the set of n×m average values of the potential energy function to obtain, for each conformational parameter, the value of that parameter that corresponds to the lowest average value of the potential energy function, which is followed by using set of n values of the n conformational parameters, one value to each parameter, to define best conformation of said molecule having lowest value of potential energy function.

k) confirming the results or locating another optimal structure, if required, by choosing a different way of arranging the values of the conformational parameters and repeating steps e to k.

In one embodiment of the invention, the method comprises obtaining optima of several simple non-linear functions each with a single known optimum in parameter range.

In another embodiment of the invention, the method is carried out by finding the best value of different types of functions of many parameters.

In a further embodiment of the invention, the method is carried out by obtaining the best structure of small molecules such as peptides, nucleotides, etc.

In a further embodiment of the invention, the method is carried out by obtaining the best structure of biological macromolecules such as proteins and nucleic acids, etc.

In another embodiment of the invention, the method runs in parallel on several computers simultaneously to further reduce the computation time.

BRIEF DESCRIPTION OF THE ACCOMPANYING DRAWINGS

FIG. 1 is an example of a set of Mutually Orthogonal Latin Squares (MOLS) in order to better explain the method. The diagram shows an example of three MOLS of order 7, i.e. n=3, m=7, N=7. Symbols in the first Latin Square: a1, a2, a3, a4, a5, a6, a7. Each of these is repeated 7 times to give a total of 49 symbols, which have been arranged in an LS. Symbols in second LS: b1, b2, b3, b4, b5, b6, b7. The second LS is orthogonal to the first. Note that every pairing of a symbol from the first Square with one from the second occurs exactly once. Symbols in third LS: c1, c2, c3, c4, c5, c6, c7. This is orthogonal to both the other Squares. For clarity in this FIG. 3 different sets of N symbols have been used. One can use the same set of N symbols and construct N−1 MOLS of order N. One of sub-squares of the set of MOLS has been highlighted, its symbols are a7 of the first LS, b1 of the second LS and c5 of the third LS. In the present application, each such sub-square represents a possible conformation of the molecule. The MOLS method requires the potential function to be evaluated at all these $N^2$ points in the conformation space.

FIGS. 5a and 5b show two minimum energy structures of the pentapeptide (Aib)$_5$ as obtained by the present MOLS method (in green). The values of the potential energy function for these structures are 5.19 kcal/mole and 9.41 kcal/mole respectively. For comparison these two structures are superimposed on the structures (in red) of the same molecule as obtained experimentally by Benedetti et al. and reported in Journal of the Chemical Society, volume 104, pages 2437–2444, and by Shamala et al. and reported in Journal of Chemical Society, Chemical Communications, year 1978 page 996. The comparison shows the present MOLS method yields correct structures. These two structures along with 998 others were identified in total time of less than 1 hour using Pentium III processor at 650 MHz.

DETAILED DESCRIPTION OF THE INVENTION

Figure 1:
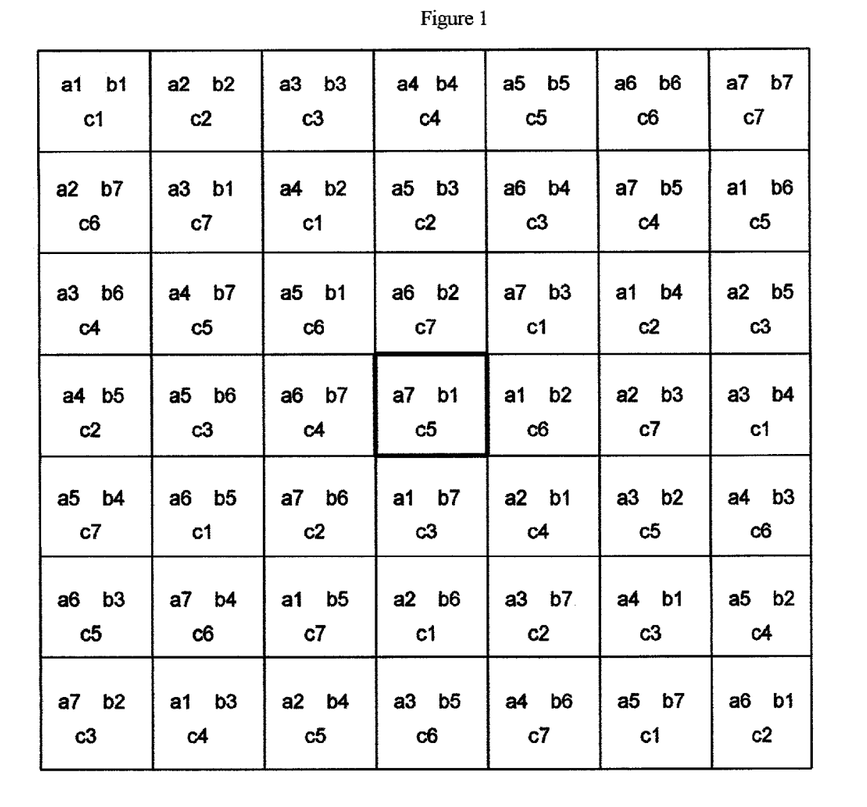

The method of the invention is best explained in terms of a series of steps. The construction of the set of MOLS comprises a Latin Square (LS) of order N defined as a set of N symbols, arranged in a N×N square, such that each symbol occurs exactly once in every row and once in every column. Two LS are orthogonal if, when they are superimposed, each symbol of the first square occurs once, and only once, with each symbol of the second square. A set of MOLS is a set of LS, every pair of which is orthogonal (FIG. 1). It has been shown in the prior art that if N is a prime power, one can construct N−1 MOLS of order N, as follows. The N symbols (belonging to a Galois field) are written as $b_i$, i=1 to N. If is the (i, j)$^{th}$ element of the LS labeled by e, then $$a_{ij}^e = b_e \times b_i + b_j \qquad (1)$$

for i=1 to N; j=1 to N; e=1, N−1. In the present algorithm a correspondence is made between the symbols b and the conformational parameters of the molecule. For example, these may be the torsion angles, $\theta_i$, i=1 to n, which characterize the conformation of an oligopeptide. The best conformation of the molecule is defined to be the one, which has the minimum value of the potential energy function, which is a function of the conformational parameters. In other words if the set of conformational parameters that will yield a minimum value to the potential energy function is found, then that set of conformational parameters will correspond to the best conformation of the molecule. Each conformational parameter is specified as being capable of taking up m different values in a particular range. If r is the index for these conformational parameters and s is the index for the values taken up by each parameter, then $\theta_{r,s}$, r=1 to n; s=1 to m are the input set of values, and the search for the best conformation has to be carried out among the $n^m$ combinations of these values. Thus, for example, $\theta_{1,1}$ could refer to the first value of the first parameter, $\theta_{1,2}$ to the second value of the first parameter, $\theta_{2,1}$ to the first value of the second parameter, $\theta_{2,2}$ to the second value of the second parameter, and so on up to $\theta_{n,m}$, which would refer to the last value of the last parameter. Obviously there would be a set of m×n input values. To construct the set of MOLS, each conformational parameter is set to correspond to one LS, and apply equation (1) to the indices of the conformational parameters. The indices r and s are considered to form n Galois sets, each with m elements, i.e. the index pair (r,s) will form the s$^{th}$ element in the r$^{th}$ set. The sub-squares of the MOLS are labeled by the pair of indices (u,t), with both u and t taking up integer values from 1 to N, the value of the r$^{th}$ torsion angle in the sub-square (u,t) may be chosen from the input set of values $\theta_{r,s}$ as $$\theta_{u,t}^r = \theta_{r,s}$$

where the index u is given by u={(t−1)(r−1)+(s−1)} modulo( N) The value of N is chosen such that (i) N−1 ≧ maximum (m,n) and (ii) N is a prime power. This last condition requires that in practice the step size in the sampling grid is chosen to be R/N, where R is the specified range for the conformational parameters. The application of this procedure for all values of r=1 to n; s=1 to N and t=1 to N will result in a set of n MOLS of order N. These MOLS, when superposed, will give $N^2$ sub-squares, each sub-square containing a set of values for the n conformational parameters (FIG. 1). Each set of values of the parameters, labeled by the index pair (u,t), represents one possible conformation of the polypeptide chain and, therefore, a point in the n dimensional conformational space. The method of the present invention shows that sampling the potential surface of the molecule at the $N^2$ points specified by the sub-squares, out of the possible $n^m$, is sufficient to build a map of the entire space, and that this map can then be used to perform a rapid search for the optimum. The hypothesis is supported by the fact that the set of MOLS implicitly contains every possible two-dimensional projection of the n-dimensional space. The next step is the sampling of the energy hyper-surface in conformational space, which is carried out by calculating the potential energy $$V_{u,t} = V(\theta^r_{u,t})$$

at each of the $N^2$ points u=1 to N; t=1 to N. After this step is completed and the $N^2$ values of the potential energy function have been calculated, the next task is to recover the energy map of the conformational space. To accomplish this n one-dimensional representations of the variation of the potential energy function V along each of the conformational parameters is constructed. The effect of setting a particular conformational parameter to a particular value is estimated by taking the average of V over the N points where that value of that parameter occurs in the MOLS, i.e.

$$<V>^r_s = \frac{\sum_t V(\theta^r_{u,t})\exp(-V(\theta^r_{u,t})/\kappa T)}{\sum_t \exp(-V(\theta^r_{u,t})/\kappa T)};$$

where k is Boltzmann's constant and T is the temperature. Once again, equation (2) is used to calculate the value of u for each value of r, s and t. Since the number of steps m along each parameter are set as equal to N, there will be N such average values for each of the r=1 to n conformational parameters. The N average values for a given parameter will form a representation of the behavior of the potential V as a function of that parameter. The final step is an inspection of each one-dimensional representation, which will therefore reveal the optimum value for the respective torsion. Thus, if $$V^r_{s=\omega_r} = \underset{\text{over } s}{\text{optimum}} \left(\langle V \rangle^r_s\right) \quad (3)$$

then $\theta_{r,\omega_r}$ is the optimum value for the parameter r. The set of optima $\theta_{r\omega_r}$ r=1 to n will then define the optimum conformation of the molecule. This completes the procedure.

The indices r and s used in the construction of the MOLS may be assigned to the m values of the n parameters in $(m!)^n$ different ways. According to the invention no matter which way the assignment is made, the procedure will result in an optimal structure. Therefore, by choosing different assignments of the angles, the calculations may be repeated to check for the consistency of the results obtained.

Novelty vis-à-vis Prior Art:
1. Mutually Orthogonal Latin Squares (MOLS) have not been previously used to find the best molecular or biomolecular structure.
2. MOLS have not been previously used to find the best value of a function.
3. MOLS have not been previously used to find the global best value of a function.
4. Equation 2 has not been previously stated or used.
5. The method of taking averages as given in equation (3) has not been previously used.

The following examples are given by way of illustration of the present invention and should not be construed to limit the scope of the present invention.

EXAMPLE 1

Figure 2A:
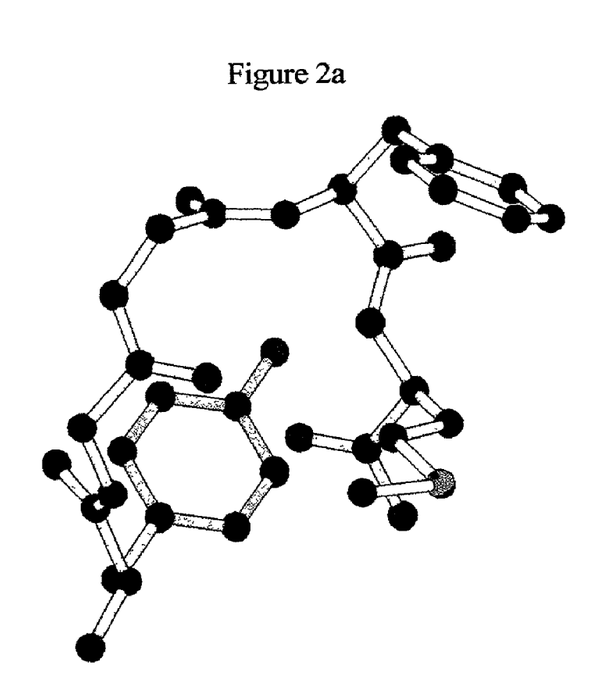
FIG. 2a gives the structure of the molecule pentapeptide [Met$^5$] enkephalin (Tyr-Gly-Gly-Phe-Met) as obtained by an application of the present MOLS method as described in example 1. The value of the potential energy function for this structure is −13.61 kcal/mole.
Figure 2B:
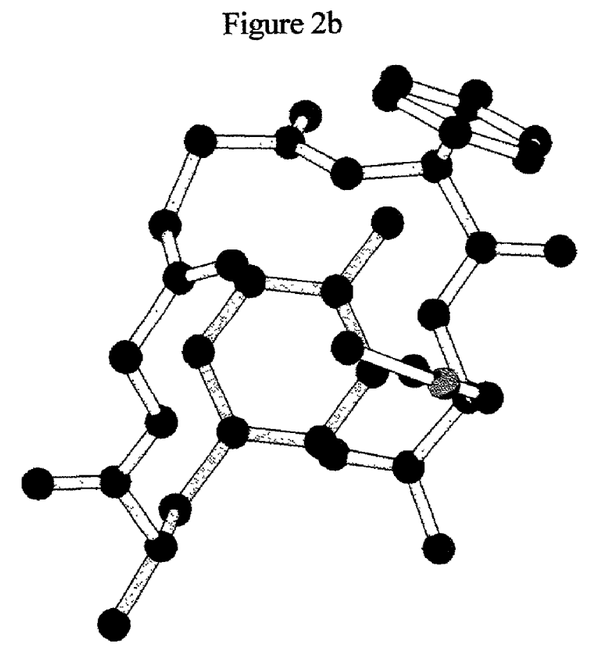
FIG. 2b shows for comparison the structure of the molecule as reported by Z. Li and H. A. Scheraga in the Proceedings of the National Academy of Sciences (USA), Volume 84, pages 6611–6615. It is clear from the comparison that the two structures are the same and that the present MOLS method successfully identifies the correct structure of the molecule. The present MOLS method identified this structure and 99 other structures in a total computation time of 65 seconds on a Pentium III processor running at 650 MHz. This time is far less than the time taken by the procedure of Li and Scheraga.
Figure 3A:
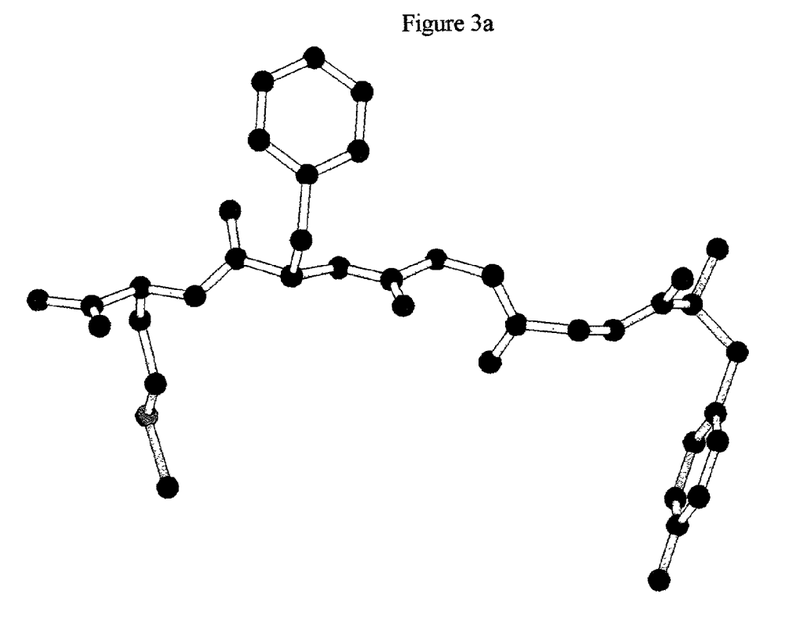
FIG. 3a shows another structure of the molecule pentapeptide [Met$^5$] enkephalin (Tyr-Gly-Gly-Phe-Met) as obtained by application of the present MOLS method as described in example 1. Value of potential energy function for this structure is −8.53 kcal/mole.
Figure 3B:
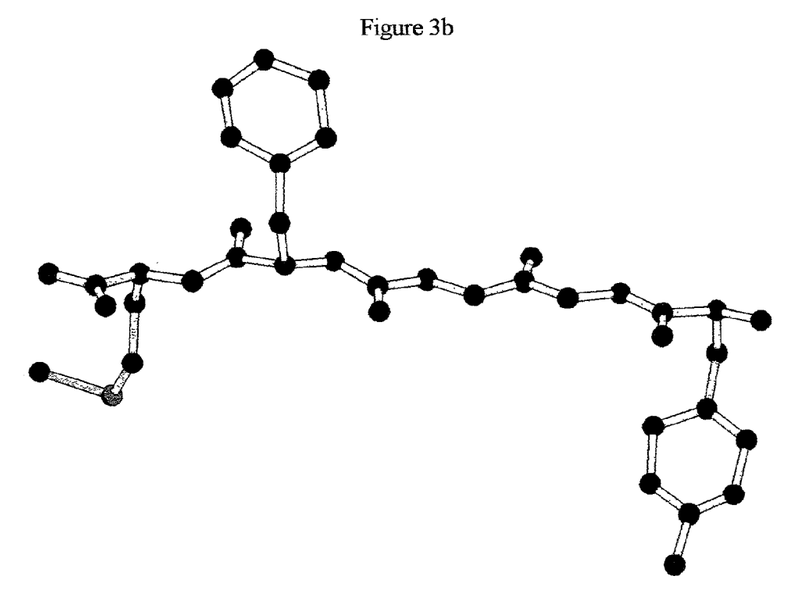
FIG. 3b shows for comparison the experimentally determined structure of the molecule as reported by Griffin, et al., in Proceedings of the National Academy of Sciences (USA), volume 83, pages 3272–3276. It is clear from the comparison that the two structures are the same and that the present MOLS method successfully identifies the correct structure of the molecule. The present MOLS method identified this structure and 99 other structures, including the one shown in drawing 2 above, in a total computation time of 65 seconds on a Pentium III processor running at 650 MHz.
Figure 4:
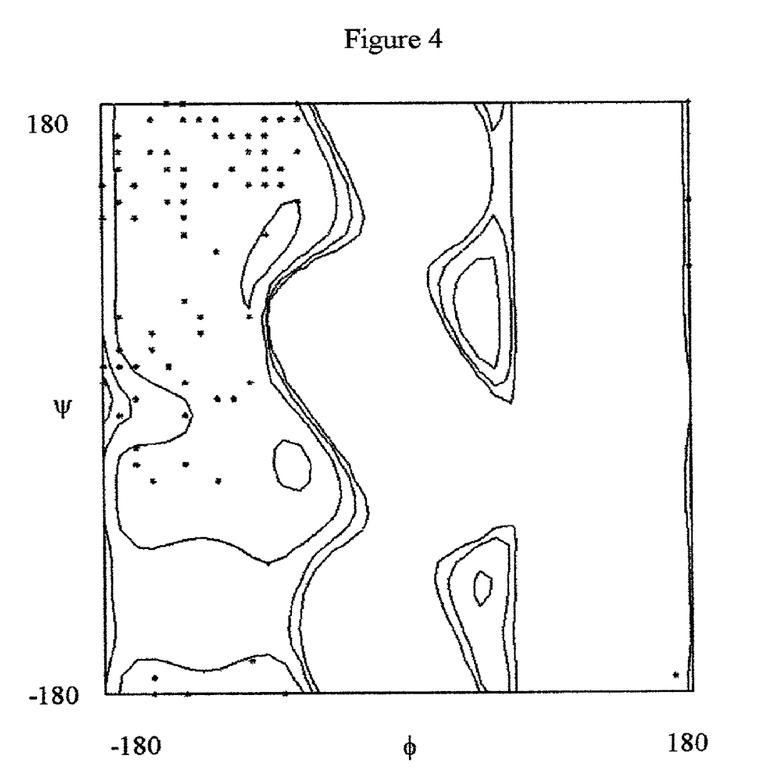
FIG. 4 shows Ramachandran plot for one hundred different structures, including the structures shown in FIG. 2 and in FIG. 3 above, obtained by repeating the method with a different set of input values each time. The drawing clearly shows that all structures are conformationally best structures as tested by the Ramachandran map, since their conformations all correspond to the allowed regions of the Ramachandran map.

As an example the method of the invention is applied to pentapeptide [Met$^5$] enkephalin (Tyr-Gly-Gly-Phe-Met). Ignoring the side chain torsion angles, which were kept fixed at the values found in the literature, there are 8 backbone torsion angles. These are considered the conformational parameters, with range between 0 and 360°. To sample each of them at intervals of 10° would require 36 points along each dimension. The total search space is thus $36^8$ or about $2.8 \times 10^{12}$ points and an exhaustive search for the optimal structure would entail the calculation of the energy at each of these points to choose the best one. In the present method the energy is calculated at only $36^2$ points. However since the order of MOLS is always a prime number and since 36 is not a prime number, in reality $37^2$ points are searched. As the first step the set of values for each torsion angle that is to be considered is specified. Thus the values for the first torsion angle may be 0°, 10°, 20°, 30°, .360°. Similarly the second torsion angle has to be considered at the values 0°, 10°, .360°. Likewise the sampling points of the other torsion angles are also specified. Thus, the values $\theta_{r,s}$ for r=1,8; s=1, 37 are specified. Equation (2) is now used to distribute 37 copies of these 37 values of each of the 8 torsion angles among the $37^2$ sub squares so as form a set of 8 Mutually Orthogonal Latin Squares of order 8. The 8 values in each sub square will then form one possible conformation of the molecule. Note that some of these conformations may be 'impossible' conformations, in the sense that the atoms may interpenetrate. However, the present invention allows one to derive the optimal conformation from this set of $37^2$ conformations. The next step in the procedure is to calculate the semi-empirical potential energy at each of these $37^2$ points. Once these energies have been calculated, the next step comprises ascertaining the average energy for each value of each torsion angle. For example, for the first value of the first torsion angle this is 0°. There are 37 conformations of the molecule in which the value of the first torsion angle has been set to 0° and the values of the potential energy function of all these conformation have been determined in the procedure above. The Boltzmann weighted average of these 37 energy values is taken, and thus a single number obtained which specifies the effect of setting this angle to this value, i.e. the effect of setting the first torsion to the value 0°. Similarly the average energy when the first torsion is set to 10°, 20°, etc is obtained. It is important to note that it is the property of MOLS that each setting is repeated 37 times (or N times, where N is the order of the MOLS). Since there are 37 settings for the torsion, there will be 37 average energies. The next step comprises inspecting these 37 averages and identifying one setting of this torsion that has yielded the lowest average energy. This will be the optimum value for this torsion angle. The procedure is repeated for the next torsion angle and the optimum value for this also determined in an exactly similar manner as for the first one. Note that again, due to the property of the MOSL, each value of the second torsion also will be repeated 37 times. The whole procedure is again repeated for the other torsion angles. At the end of this step the invention has individually determined the best setting for each of the 8 torsion angles. When the molecule is now constructed with these 8 torsion angle values, identified by the invention, this will be the optimal conformation of [Met$^5$] enkephalin. The entire procedure is repeated by choosing $\theta_{r,s}$ in a different way. Now instead of specifying $\theta_{1,1}$=0.0, $\theta_{1,2}$=10.0 etc, the specified values for $\theta_{1,1}$=10.0, $\theta_{1,2}$=0.0 etc. The assignments are made using a random number generator. The steps are repeated to yield another optimal conformation for the molecule. This may be repeated again and again to yield as many optimal structures as required. In this example, one hundred optimal structures were generated. Each structure was the result of the application of the above procedure to a different input set of torsion angles $\theta_{r,s}$, which was obtained by a different assignment of the indices to the torsion angle values. The assignments were chosen using a random number generator. The energies corresponding to all these structures are low, the highest being 72.3 kcal/mole and the lowest −14.0 kcal/mole, with an average of −7.34 kcal/mole for all 100 structures. The best structure is shown in FIG. 2 and FIG. 3 and the conformational Ramachandran Plot of all 100 structures shown in FIG. 4.

EXAMPLE 2

As another example the invention, to shown its application for arbitrary functions and not just for potential energy functions based on conformational parameters, the method is applied to an artificial function with a known minimum as follows:

$$F=2^{(a-5)} \times 3^{|b-2|} \times 4^{|c-9|} \times 5^{|d-6|} \times 6^{|e-8|} \times 6^{(f-8)} \times 5^{(g-6)} \times 4^{(h-9)} \times 3^{(i-2)} \times 2^{|j-5|} \times (k-7.1)^4$$

This is a function of the 11 variables a, b, c, d, e, f, g, h, i, j, k all of them sampled in the range 1.0 to 13.0, in steps of 1.0. The minimum of the function in this space is at a=1.0, b=2.0, c=9.0, d=6.0, e=8.0, f=1.0, g=1.0, h=1.0, i=1.0, j=5.0, k=7.0. A set of 11 MOLS of order 13 is constructed using the values 1.0, 2.0, . . . 13.0 as range of values for each of the 11 variables. The function is evaluated at each of the points specified by the 13×13 sub squares. Averages are taken and the minimum is identified as 1.0, 1.0, 8.0, 5.0, 8.0, 2.0, 1.0, 1.0, 1.0, 5.0, 7.0. This result is very close to the theoretical minimum given above.

EXAMPLE 3

Figure 5A:
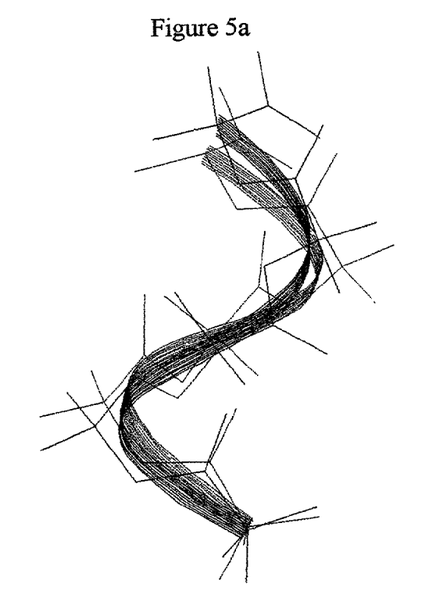
Figure 5B:
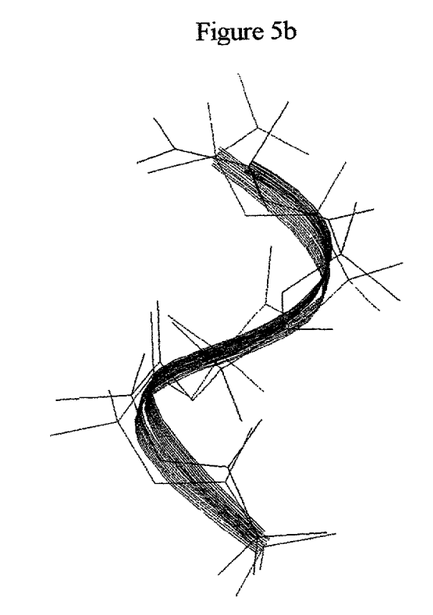
Figure 6:
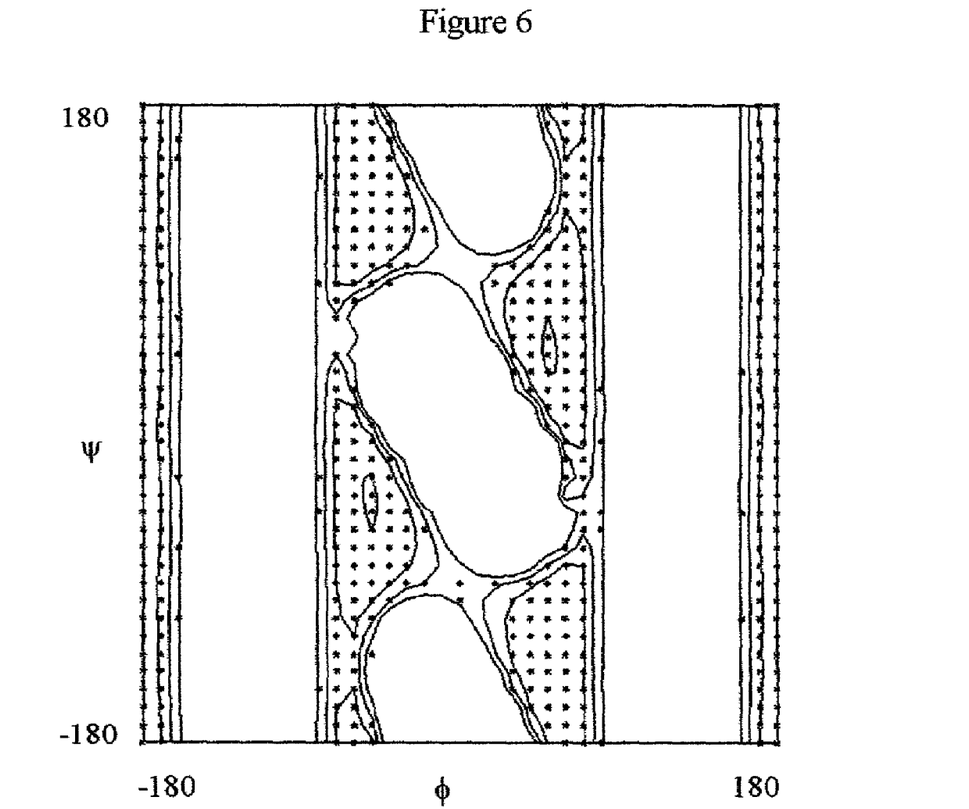
FIG. 6 shows the Ramachandran plot for one thousand different structures, including the structures shown in FIG. 5 above, obtained by the present MOLS method, by repeating the method with a different set of input values each time. The drawing clearly shows that all structures are conformationally best structures as tested by the Ramachandran map, since their conformations all correspond to the allowed regions of the Ramachandran map. These 1000 structures were obtained in a total time of less than 60 minutes on Pentium III processor running at 650 MHz.
Figure 7:
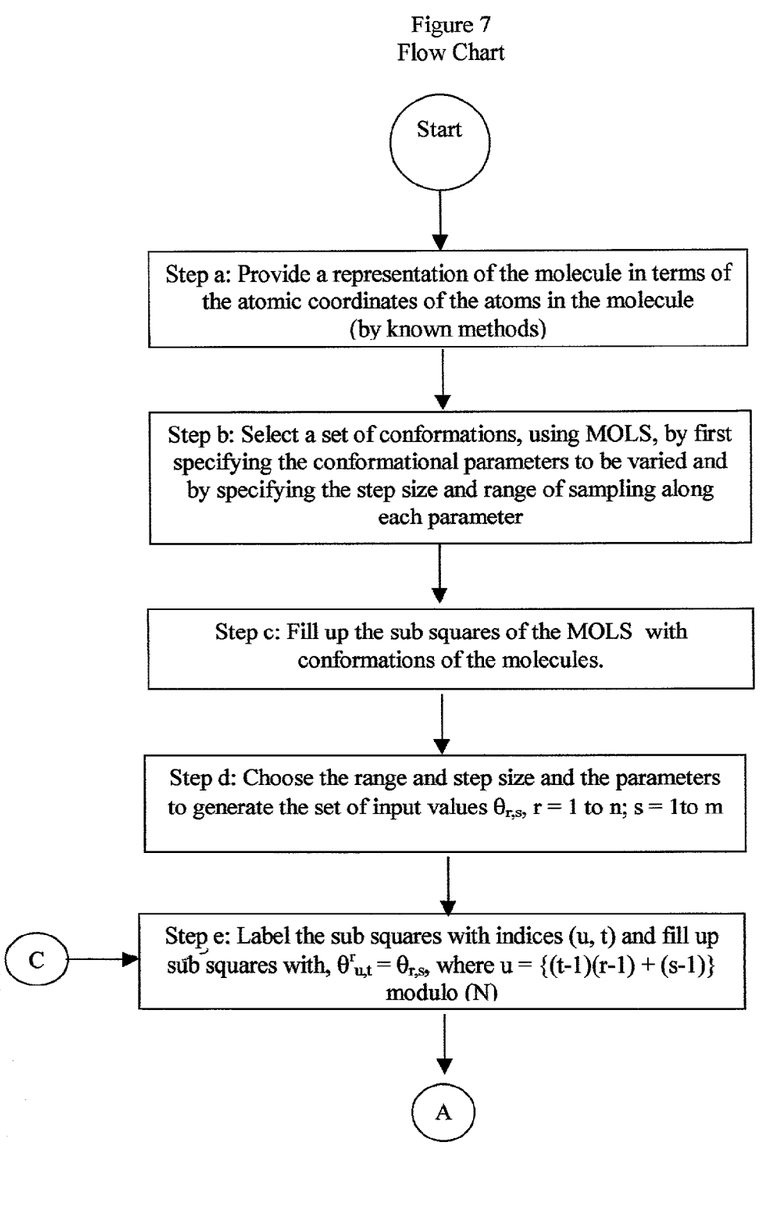
FIG. 7 gives a detailed flowchart to explain the procedure.

In this example, the molecule chosed comprises the pentapeptide (Aib)$_5$. An in example 1, the number of free torsion angles in this molecule is 8. Again these are chosen as the conformational parameters, with the range set to 0 to 360°. At steps of 10° there are 37 points along each dimension and order of the MOLS is chosen as 37. The 37$^2$ conformational points are specified using MOLS, the potential energy functions are calculated, averages are taken and optimal conformation is identified as described in example 1. This is repeated 1000 times in a total computer time of about 1 hour for all 1000 conformations. All of them are good conformations as seen by the low energy values. Some of them correspond to well known structures such as alpha helices or turns. FIG. 5 shows the best two structures and FIG. 6 shows the Ramachandran conformational plot of all 1000 structures.

Summary of observations: The invention works very well for different types of functions. Particularly in molecular conformation analyses, the invention allows one to map the entire conformational space in a reasonable amount of time, to identify physically reasonable structures.

The Main Advantages of Present Invention Are
1. The main advantage of the present invention is that it provides a method to build optimal 3-dimensional models of molecular structures from knowledge of their chemical structures, which obviates the drawbacks of the previous methods.
2. Another advantage of the present invention is that it provides a method and system to build minimum-energy structures of biological macromolecules such as proteins and nucleic acids.
3. Another advantage of the present invention is that it may be applied to find the best value of a function.
4. Another advantage of the present invention is that it may be applied to find the best value of a potential energy function of a molecule.
5. Another advantage of the present invention is that it is simple and straightforward and inexpensive, in terms of computer time, to use.
6. Another advantage of the present invention is that it may be applied to a wide variety of problems in which a physical or chemical system is defined as a function of a set of parameters and the invention is used to find the best configuration of the system by finding the best set of values of the parameters which give the best value of the function.
7. Another advantage of the present invention is that it may be combined with other known methods such as gradient search, simulated annealing, etc.
8. Another advantage of the present invention is that it may be easily programmed to run on parallel computers, thus saving valuable time.

We claim:
1. A method for modeling the three dimensional structure of a molecule by determining the lowest value of conformational potential energy of a molecule by using an algorithm to define the lowest value of the conformational potential energy as the best conformation representing the three dimensional structure of the molecule, said algorithm comprising the steps of:
   a) representing the molecule in terms of coordinates defined by torsion angles of the atoms comprising the molecule;
   b) specifying the number of torsion angles, n, the range of each n torsion angle, and a step size at which the values of each torsion angle is sampled, there being a total of m steps for each torsion angle, $\theta_{r,s}$, r=1 to n and s=1 to m as the input set of values for each torsion angle selected;
   c) selecting a set of all possible conformations of the molecule represented by a combinatorial arrangement of Mutually Orthogonal Latin Squares (MOLS) of order N, wherein said MOLS are constructed based upon the n selected torsion angles of the molecule to provide $N^2$ sub squares in each set of MOLS, wherein N is a prime number obtained by R/m, R being 360°, with each MOLS sub square corresponding to one possible conformation of the molecule;

d) labeling the sub squares of the MOLS by indices (u,t), u and t being integer numbers, u=1 to N and t=1 to N, and the value of the rth torsion angle in a given sub square (u,t) being chosen from the input set of values $\theta_{r,s}$ as $$\theta_{u,t}^r = \theta_{r,s}$$

in which the index u is given by u={(t−1)(r−1)+(s−1)} modulo(N);

e) repeating the procedure of filling up the sub squares of the MOLS with the values chosen for r=1 to n, s=1 to m, and t=1 to N, with u being calculated each time by the formula given in step (d), until each sub square of the $N^2$ MOLS sub squares are filled with a set of n values, each value defining one conformation of the molecule, resulting in $N^2$ conformations;

f) calculating the potential energy for each of $N^2$ conformations of the molecule in accordance with $$V_{u,t} = V(\theta_{u,t}^r),$$

g) analyzing the set of $N^2$ values obtained to determine a best value for each torsion angle, by determining the average value of the potential energy for each torsion angle at all the N conformations, there being n×m average values, the set of average values being determined according to the formula:

$$<V>_s^r = \frac{\sum_t V(\theta_{u,t}^r)\exp(-V(\theta_{u,t}^r)/\kappa T)}{\sum_t \exp(-V(\theta_{u,t}^r)/\kappa T)};$$

h) scanning the set of n×m average values of the potential energy obtained for each torsion angle, to determine the lowest average value of the potential energy to define a best conformation of the molecule;

i) confirming the results obtained by choosing a different set of values for the torsion angle and repeating steps e) to i); and j) outputting the best conformation of the molecule to a user of said method.

2. A method according to claim 1, wherein a single best value for the torsion angle is used to calculate the indices (u,t) for labeling the MOLS sub squares, the potential energy $$V_{u,t} = V(\theta_{u,t}^r),$$

and average value of potential energy according to the formula set forth in step g).

3. A method according to claim 1 wherein the molecule is a small molecule selected from the group consisting of peptides and nucleotides.

4. A method according to claim 1 wherein the molecule is a macromolecule selected from the group consisting of proteins and polynucleic acids.

5. A method according to claim 1 wherein the calculations are conducted in parallel by employing several computers for the calculations.

* * * * *